US00PP27552P2

(12) United States Plant Patent
Wezelenburg

(10) Patent No.: US PP27,552 P2
(45) Date of Patent: Jan. 17, 2017

(54) ***VIBURNUM* PLANT NAMED 'JWW 5'**

(50) Latin Name: *Viburnum plicatum*
Varietal Denomination: JWW 5

(71) Applicant: Jan-Willem Wezelenburg, Hazerswoude-Dorp (NL)

(72) Inventor: Jan-Willem Wezelenburg, Hazerswoude-Dorp (NL)

( * ) Notice: Subject to any disclaimer, the term of this patent is extended or adjusted under 35 U.S.C. 154(b) by 182 days.

(21) Appl. No.: 14/121,533

(22) Filed: Sep. 16, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Penny J. Aguirre

(57) ABSTRACT

A new cultivar of *Viburnum plicata* plant named 'JWW 5' that is characterized by its dense and distinct upright plant habit, its sterile flowers that blushed pink in color, its young stems that are red in color, and its well-developed fruits that are large, glossy and red in color.

3 Drawing Sheets

Botanical classification: *Viburnum plicatum.*
Variety denomination: 'JWW 5'.

BACKGROUND OF THE INVENTION

The present invention relates to a new and distinct cultivar of *Viburnum plicatum*. The new *Viburnum* will hereafter by its cultivar name, 'JWW 5'. 'JWW 5' is a new cultivar of deciduous shrub grown for use as an ornamental landscape plant.

The new cultivar is the result of a controlled breeding program conducted by the Inventor in Hazerswoude-Dorp, The Netherlands. The objective of the breeding program was to develop a new cultivar of *Viburnum plicatum* that is pink flowering with an upright plant habit.

The new cultivar arose from a cross made by the Inventor in Barmstedt, Germany in spring of 2009 between *Viburnum plicatum* 'JWW1' (U.S. Plant Pat. No. 22,326) as the female parent and *Viburnum plicatum* 'Pink Beauty' (not patented) as the male parent. The Inventor selected 'HJWW5' as a single unique plant amongst the seedlings that resulted from the above cross in spring of 2011.

Asexual propagation of the new cultivar was first accomplished by the Inventor using softwood stem cuttings in June of 2011 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JWW 5' as a unique cultivar of *Viburnum.*

1. 'JWW 5' exhibits a dense and distinct upright plant habit.
2. 'JWW 5' exhibits sterile flowers that blushed pink in color and fade to white.
3. 'JWW 5' exhibits young stems that are red in color.

4. 'JWW 5' exhibits well-developed fruits that are large, glossy and red in color.

'JWW1', the female parent of 'JWW 5', differs from 'JWW 5' in having sterile flowers that are white in color and in producing less fruits. 'Pink Beauty', the male parent of 'JWW 5', differs from 'JWW 5' in having sterile flowers that deeper pink in color, a less upright and broader plant habit, and in producing smaller fruits. 'JWW 5' can be most closely compared to *Viburnum plicatum* cultivars 'Lanarth' (not patented) and 'Watanabe' (not patented). 'Lanarth' is similar to 'JWW 5' in flower form and in freely producing fruit. 'Lanarth' differs from 'JWW 5' in having a more open and less upright plant habit, in having white sterile flowers, and in producing smaller fruit that ripen earlier in the season. 'Watanabe' is similar to 'JWW 5' in flower form and plant habit. 'Watanabe' differs from 'JWW 5' in having a slower growth rate and in having white sterile flowers.

BRIEF DESCRIPTION OF THE DRAWINGS

The accompanying colored photographs illustrate the overall appearance and distinct characteristics of the new cultivar. The plant in the photographs is about 1.5 years in age as grown outdoors in a 19-cm container in Hazerswoude-Dorp, The Netherlands.

The photograph in FIG. 1 provides a side view of 'JWW 5' in bloom.

Figure 1:
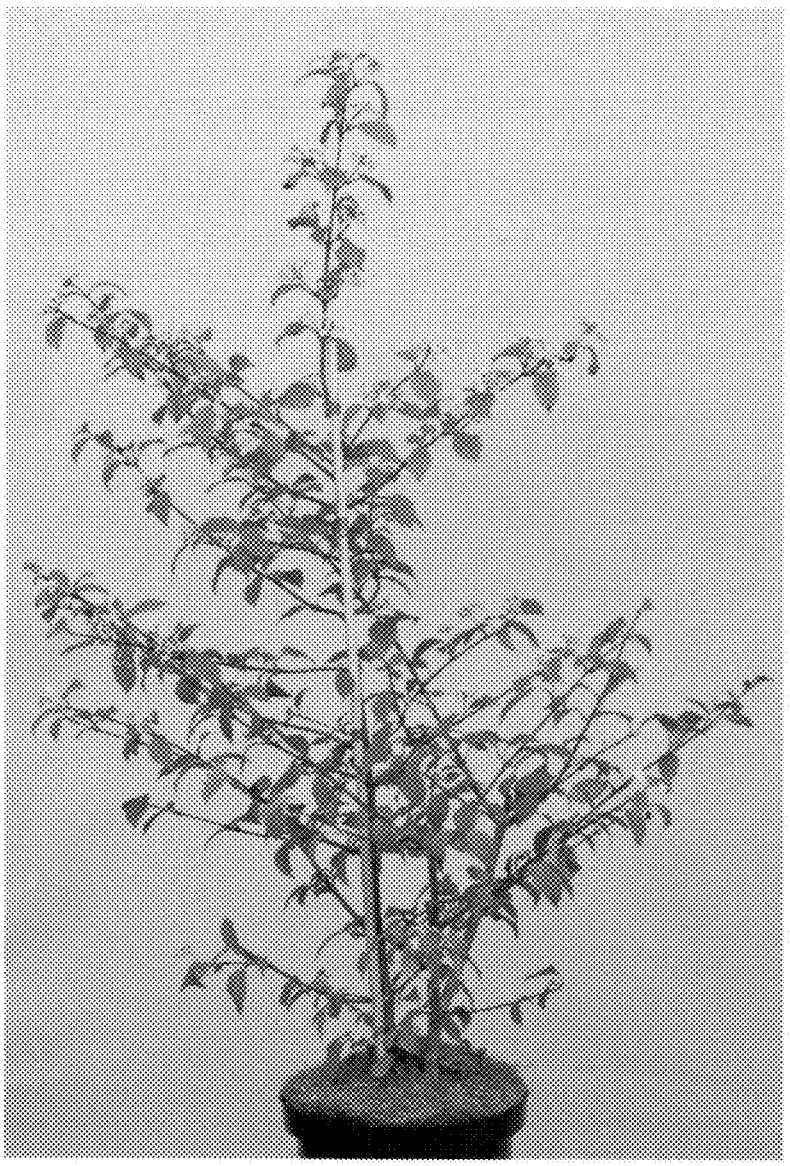
Figure 2:
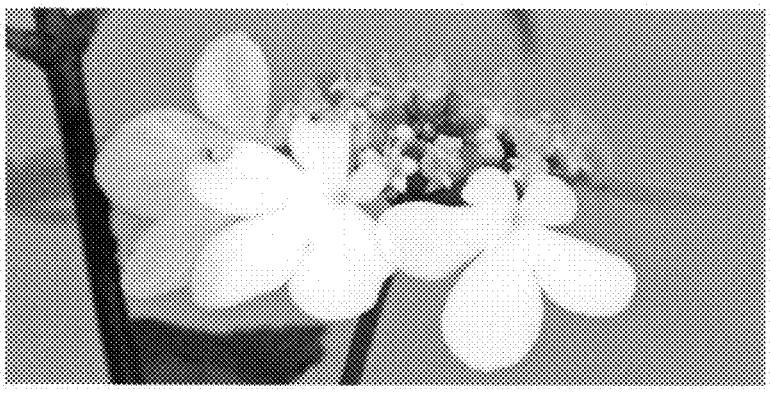

The photograph in FIG. 2 provides a view of the fading flowers of 'JWW 5'.

Figure 3:
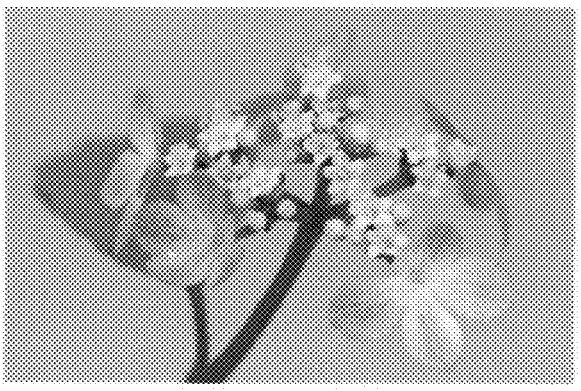

The photograph in FIG. 3 provides a view of the newly opened flowers of 'JWW 5'.

Figure 4:
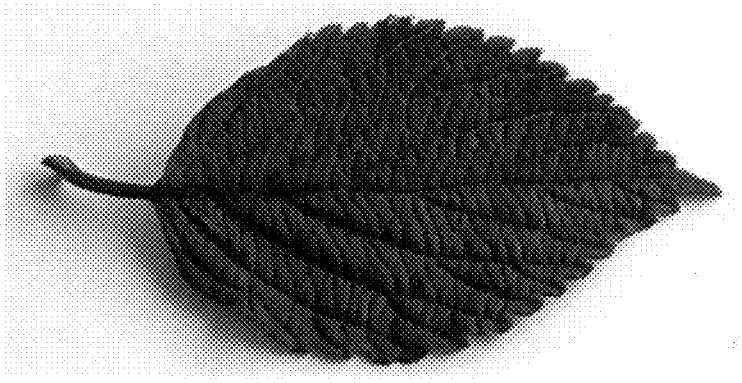

The photograph in FIG. 4 provides a close-up view of a mature leaf of 'JWW 5'.

Figure 5:
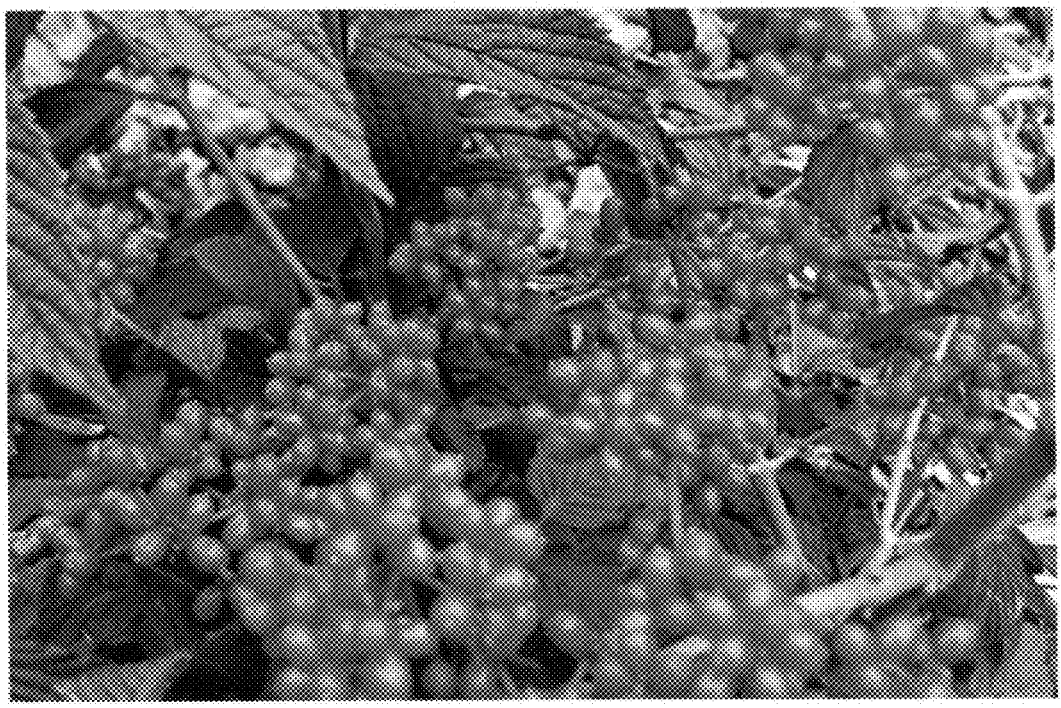

The photograph in FIG. 5 provides a view of the fruit of 'JWW 5'.

The colors in the photograph may differ slightly from the color values cited in the detailed botanical description, which accurately describe the colors of the new *Viburnum.*

DETAILED BOTANICAL DESCRIPTION

The following is a detailed description of 1.5 year-old plants of the new cultivar as grown outdoors in 19-cm containers in Hazerswoude-Dorf, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Perennial shrub.

*Plant habit.*—Narrow, dense, distinctly upright.

*Plant shape.*—Narrow ovate.

*Plant size.*—Reaches about 2 m in height and 1 m in spread in the landscape.

*Cold hardiness.*—At least in U.S.D.A. Zones 5.

*Diseases and pests.*—No susceptibility or resistance to diseases or pests has been observed.

*Root habit.*—Fibrous.

*Propagation.*—Softwood stem cuttings.

*Growth rate.*—Moderate.

*Root development.*—Roots initiate in about 3 weeks and fully develop as a young rooted plant in about 3 months.

Stem description:

*Shape main stem and lateral branches.*—Rounded.

*Man stem and lateral branch color.*—Young branches; 148D, upper side slightly tinged 182C, mature branches; ranging between 199C and N199A.

*Main stems.*—An average of 1 m in length and 5 mm in diameter.

*Lateral branch size.*—An average of 35.4 cm in length (excluding the inflorescence) and 2.5 mm in diameter.

*Main stem and lateral branch surface texture.*—Slightly glossy.

*Lateral branch strength.*—Moderately strong.

*Branching.*—Average of 29 lateral branches, freely branching.

*Lateral branch internode size.*—Average of 5.7 cm.

Foliage description:

*Leaf shape.*—Ovate to elliptic.

*Leaf division.*—Single.

*Leaf base.*—Rounded.

*Leaf apex.*—Apiculate.

*Leaf fragrance.*—None.

*Leaf venation.*—Pinnate, 148C, tinged towards the base 183B in color on upper surface, 145B to 145C in color on lower surface.

*Leaf margins.*—Serrate.

*Leaf arrangement.*—Opposite.

*Leaf attachment.*—Petiolate.

*Leaf surface.*—Both surfaces moderately rugose, veins furrowed and moderately glossy.

*Leaf size.*—An average of 7.7 cm in length and 4.5 cm in width.

*Leaf quantity.*—An average of 14 (7 pairs) per branch.

*Leaf color.*—New growth upper surface; 143A, new growth lower surface; ranging between 137D and 143A, mature growth upper surface; N137A, mature growth lower surface 138A.

*Petioles.*—Average of 1.2 cm in length and 2 mm in width and 152D in color, slightly glossy surface.

Flower description:

*Blooming period.*—Blooms continuously from mid-May to October in the Netherlands.

*Inflorescence type.*—Flattened cyme of fertile and sterile flowers.

*Lastingness of inflorescence.*—Average of 10 days.

*Inflorescence size.*—Average of 2 cm in height and 5.1 cm in width.

*Inflorescence number.*—Average of 6 sterile flowers and 45 fertile flowers.

*Flower number.*—An average of 27 sterile flowers and 200 fertile flowers per lateral system.

*Flower fragrance.*—None.

*Flower aspect.*—Upright.

*Flower size.*—Sterile flowers; an average of 2.4 cm in diameter and 7 mm in depth, fertile flowers; an average of 5 mm in diameter and 6 mm in depth.

*Flower buds.*—Sterile flowers; an average of 2 mm in length and 2 mm in width, globular in shape, 150C, tinged 31D at the tips in color, fertile flowers; an average of 2 mm in length and 2 mm in width, globular in shape, NN155A in color.

*Peduncles.*—Medium strength, average of 2.7 cm in length and 1.5 mm in width, 180C in color, surface is glabrous and slightly glossy, held at an angle of 40°.

*Pedicels.*—Sterile flowers; moderate strength, an average of 6 mm in length and 1 mm in width, 174C to 174D in color, surface is glabrous and slightly glossy, held at an angle of 60°, fertile flowers; moderate in strength, an average of 0.5 mm in length and 1 mm in width, 174C to 174D in color, surface is glabrous and slightly glossy, held at an angle of 45°.

*Petals.*—Fertile flowers; average of 5 petals, fused at base, ovate and convexed in shape, entire margins, obtuse apex, both surfaces smooth and dull, 2.5 mm in length, 1.5 mm in width, color; NN155C when opening and fully open on upper surface, NN155D when opening and fully open lower surface, sterile flowers; petal spot about 1 mm in diameter and 155D in color.

*Sepals.*—Sterile flowers; average of 5, fused at base, variable but primarily obovate in shape, entire margins, obtuse apex, both surfaces smooth and dull, 1.1 cm in length, 7 mm in width, color; 42D when opening on upper surface, 145B when opening lower surface, 47C to 47D when fully open upper surface, 151D, tinged 47C to 47D when fully open lower surface, upper and lower surfaces fade to NN155C to NN155D, fertile flowers; 5, fused with apex free, campanulate calyx (0.3 mm in length and 1.5 mm in width), both surfaces smooth, upper surface slightly glossy, deltoid in shape, entire margin, apex is acute, average of 0.3 mm in length and 0.6 mm in width, young and mature upper and lower surfaces 145C in color with very apex 42D.

Reproductive organs (fertile flowers):

*Stamens.*—Average of 5, anther is 1 mm in length, oval in shape and 4B to 4C in color, filament is an average of 4 mm in length and NN155C in color, pollen is moderate in quantity and 4B in color.

*Pistils.*—Average of 1, average of 1 mm in length, style is an average of 0.5 mm in length and NN155D in color, stigma is club shaped and NN155A in color, ovary is 145B to 145C in color.

*Fruit and seed.*—Well-developed drupe, oblong to elliptic in shape, 8 mm in length and 5 mm in diameter, glossy surface, 46B to 46C in color, seed; 1 per drupe, average of 4 mm in length and 2 mm in width, oval in shape, smooth texture, 163B in color.

It is claimed:

1. A new and distinct cultivar of *Viburnum* plant named 'JWW 5' as herein illustrated and described.

* * * * *